United States Patent [19]

Pernier et al.

[11] Patent Number: 4,957,116

[45] Date of Patent: Sep. 18, 1990

[54] METHOD AND DEVICE OF BRAIN'S CARTOGRAPHY IMPLEMENTED BY INTERPOLATION

[75] Inventors: Jacques Pernier, Saint Priest; Francois Perrin, Sainte Foy, both of France

[73] Assignee: Institut National de la Sante et de la Recherche Medicale, I.N.S.E.R.M., Paris, France

[21] Appl. No.: 299,153

[22] Filed: Jan. 19, 1989

[30] Foreign Application Priority Data

Jan. 19, 1988 [FR] France .............................. 88 00545

[51] Int. Cl.[5] .............................. A61B 5/04

[52] U.S. Cl. .............................. 128/731; 364/413.05

[58] Field of Search .............................. 128/731-732; 364/413.02, 413.05, 413.18, 577

[56] References Cited

U.S. PATENT DOCUMENTS 4,416,288 11/1983 Freeman .............................. 128/731

4,649,482 3/1987 Raviv et al. .............................. 128/731 X 4,753,246 6/1988 Freeman .............................. 128/731

*Primary Examiner*—Francis Jaworski

*Attorney, Agent, or Firm*—Sughrue, Mion, Zinn, Macpeak & Seas

[57] ABSTRACT

This invention relates to a method of interpolation of an electric value U at any point of a sphere, based on a finished number n of measures made at determined and known sites $P_i$.

This invention is also concerned with a device comprising processing circuits for the signals picked up at known acquisition sites, a central computer fitted with memorization and visualization means.

Applications: topography of present potentials, neurology.

7 Claims, 18 Drawing Sheets

$k_m$

| | | | | | | | | | |
|---|---|---|---|---|---|---|---|---|---|
| -183.9338 | -183.7562 | -183.5787 | -183.4012 | -183.2236 | -183.0460 | -182.8684 | -182.6909 | -182.5133 | -182.3357 |
| -182.1580 | -181.9804 | -181.8028 | -181.6252 | -181.4475 | -181.2699 | -181.0922 | -180.9146 | -180.7369 | -180.5592 |
| -180.3815 | -180.2038 | -180.0261 | -179.8484 | -179.6707 | -179.4929 | -179.3152 | -179.1374 | -178.9597 | -178.7819 |
| -178.6041 | -178.4264 | -178.2486 | -178.0707 | -177.8930 | -177.7151 | -177.5373 | -177.3595 | -177.1816 | -177.0038 |
| -176.8259 | -176.6481 | -176.4702 | -176.2923 | -176.1144 | -175.9365 | -175.7586 | -175.5807 | -175.4028 | -175.2248 |
| -175.0469 | -174.8690 | -174.6910 | -174.5130 | -174.3351 | -174.1571 | -173.9791 | -173.8011 | -173.6231 | -173.4451 |
| -173.2671 | -173.0890 | -172.9110 | -172.7330 | -172.5549 | -172.3768 | -172.1988 | -172.0207 | -171.8426 | -171.6645 |
| -171.4864 | -171.3083 | -171.1302 | -170.9520 | -170.7739 | -170.5957 | -170.4176 | -170.2394 | -170.0613 | -169.8831 |
| -169.7049 | -169.5267 | -169.3485 | -169.1703 | -168.9921 | -168.8138 | -168.6356 | -168.4574 | -168.2791 | -168.1008 |
| -167.9226 | -167.7443 | -167.5660 | -167.3877 | -167.2094 | -167.0311 | -166.8528 | -166.6744 | -166.4961 | -166.3177 |
| -166.1394 | -165.9610 | -165.7827 | -165.6043 | -165.4259 | -165.2475 | -165.0691 | -164.8907 | -164.7122 | -164.5338 |
| -164.3554 | -164.1769 | -163.9985 | -163.8200 | -163.6415 | -163.4631 | -163.2846 | -163.1061 | -162.9276 | -162.7491 |
| -162.5706 | -162.3920 | -162.2135 | -162.0349 | -161.8564 | -161.6778 | -161.4992 | -161.3206 | -161.1420 | -160.9635 |
| -160.7849 | -160.6062 | -160.4276 | -160.2490 | -160.0703 | -159.8917 | -159.7130 | -159.5344 | -159.3557 | -159.1770 |
| -158.9983 | -158.8196 | -158.6409 | -158.4622 | -158.2835 | -158.1047 | -157.9260 | -157.7473 | -157.5685 | -157.3897 |
| -157.2110 | -157.0322 | -156.8534 | -156.6746 | -156.4957 | -156.3169 | -156.1381 | -155.9593 | -155.7804 | -155.6016 |
| -155.4227 | -155.2439 | -155.0650 | -154.8861 | -154.7072 | -154.5283 | -154.3494 | -154.1705 | -153.9915 | -153.8126 |
| -153.6337 | -153.4547 | -153.2757 | -153.0968 | -152.9178 | -152.7388 | -152.5598 | -152.3808 | -152.2018 | -152.0228 |
| -151.8437 | -151.6647 | -151.4856 | -151.3066 | -151.1275 | -150.9484 | -150.7693 | -150.5903 | -150.4112 | -150.2321 |
| -150.0529 | -149.8738 | -149.6947 | -149.5155 | -149.3364 | -149.1572 | -148.9781 | -148.7989 | -148.6197 | -148.4405 |
| -148.2613 | -148.0821 | -147.9029 | -147.7236 | -147.5444 | -147.3652 | -147.1859 | -147.0067 | -146.8274 | -146.6481 |
| -146.4688 | -146.2895 | -146.1102 | -145.9309 | -145.7516 | -145.5722 | -145.3929 | -145.2135 | -145.0342 | -144.8548 |
| -144.6754 | -144.4960 | -144.3167 | -144.1373 | -143.9579 | -143.7784 | -143.5990 | -143.4196 | -143.2401 | -143.0607 |
| -142.8812 | -142.7018 | -142.5223 | -142.3428 | -142.1633 | -141.9838 | -141.8043 | -141.6247 | -141.4452 | -141.2657 |
| -141.0861 | -140.9066 | -140.7270 | -140.5474 | -140.3678 | -140.1883 | -140.0086 | -139.8290 | -139.6494 | -139.4698 |

FIG. 3a $k_m$ (cont'd)

| | | | | | | | | | |
|---|---|---|---|---|---|---|---|---|---|
| −139.2902 | −139.1105 | −138.9309 | −138.7512 | −138.5715 | −138.3919 | −138.2122 | −138.0325 | −137.8528 | −137.6730 |
| −137.4933 | −137.3136 | −137.1339 | −136.9541 | −136.7744 | −136.5946 | −136.4148 | −136.2350 | −136.0552 | −135.8754 |
| −135.6956 | −135.5158 | −135.3360 | −135.1561 | −134.9763 | −134.7964 | −134.6166 | −134.4367 | −134.2568 | −134.0769 |
| −133.8970 | −133.7171 | −133.5372 | −133.3573 | −133.1774 | −132.9974 | −132.8175 | −132.6375 | −132.4575 | −132.2775 |
| −132.0976 | −131.9176 | −131.7376 | −131.5575 | −131.3775 | −131.1975 | −131.0175 | −130.8374 | −130.6574 | −130.4773 |
| −130.2972 | −130.1171 | −129.9371 | −129.7569 | −129.5768 | −129.3967 | −129.2166 | −129.0365 | −128.8563 | −128.6761 |
| −128.4960 | −128.3158 | −128.1356 | −127.9554 | −127.7753 | −127.5951 | −127.4148 | −127.2346 | −127.0544 | −126.8741 |
| −126.6939 | −126.5136 | −126.3333 | −126.1531 | −125.9728 | −125.7925 | −125.6122 | −125.4319 | −125.2515 | −125.0712 |
| −124.8909 | −124.7105 | −124.5301 | −124.3498 | −124.1694 | −123.9890 | −123.8086 | −123.6282 | −123.4478 | −123.2674 |
| −123.0870 | −122.9065 | −122.7261 | −122.5456 | −122.3652 | −122.1847 | −122.0042 | −121.8237 | −121.6432 | −121.4627 |
| −121.2822 | −121.1016 | −120.9211 | −120.7406 | −120.5600 | −120.3794 | −120.1989 | −120.0183 | −119.8377 | −119.6571 |
| −119.4765 | −119.2959 | −119.1152 | −118.9346 | −118.7539 | −118.5733 | −118.3926 | −118.2119 | −118.0313 | −117.8506 |
| −117.6699 | −117.4892 | −117.3085 | −117.1277 | −116.9470 | −116.7662 | −116.5855 | −116.4047 | −116.2240 | −116.0432 |
| −115.8624 | −115.6816 | −115.5008 | −115.3200 | −115.1391 | −114.9583 | −114.7774 | −114.5966 | −114.4157 | −114.2349 |
| −114.0540 | −113.8731 | −113.6922 | −113.5113 | −113.3304 | −113.1494 | −112.9685 | −112.7876 | −112.6066 | −112.4257 |
| −112.2447 | −112.0637 | −111.8827 | −111.7017 | −111.5207 | −111.3397 | −111.1586 | −110.9776 | −110.7966 | −110.6155 |
| −110.4344 | −110.2534 | −110.0723 | −109.8912 | −109.7101 | −109.5290 | −109.3479 | −109.1668 | −108.9856 | −108.8045 |
| −108.6233 | −108.4422 | −108.2610 | −108.0798 | −107.8986 | −107.7174 | −107.5362 | −107.3550 | −107.1738 | −106.9925 |
| −106.8113 | −106.6300 | −106.4487 | −106.2675 | −106.0862 | −105.9049 | −105.7236 | −105.5423 | −105.3610 | −105.1796 |
| −104.9983 | −104.8169 | −104.6356 | −104.4542 | −104.2729 | −104.0915 | −103.9101 | −103.7287 | −103.5473 | −103.3658 |
| −103.1844 | −103.0030 | −102.8215 | −102.6401 | −102.4586 | −102.2771 | −102.0956 | −101.9141 | −101.7326 | −101.5511 |
| −101.3696 | −101.1881 | −101.0065 | −100.8250 | −100.6434 | −100.4618 | −100.2803 | −100.0987 | −99.9171 | −99.7355 |
| −99.5538 | −99.3722 | −99.1906 | −99.0090 | −98.8273 | −98.6456 | −98.4640 | −98.2823 | −98.1006 | −97.9189 |
| −97.7372 | −97.5555 | −97.3737 | −97.1920 | −97.0102 | −96.8285 | −96.6467 | −96.4650 | −96.2832 | −96.1014 |
| −95.9196 | −95.7378 | −95.5559 | −95.3741 | −95.1923 | −95.0104 | −94.8286 | −94.6467 | −94.4648 | −94.2829 |

FIG. 3b $k_m$ (cont'd)

| | | | | | | | | | |
|---|---|---|---|---|---|---|---|---|---|
| -94.1010 | -93.9191 | -93.7372 | -93.5553 | -93.3734 | -93.1914 | -93.0095 | -92.8275 | -92.6455 | -92.4635 |
| -92.2815 | -92.0996 | -91.9175 | -91.7355 | -91.5535 | -91.3715 | -91.1894 | -91.0073 | -90.8253 | -90.6432 |
| -90.4611 | -90.2790 | -90.0969 | -89.9148 | -89.7327 | -89.5506 | -89.3684 | -89.1863 | -89.0041 | -88.8219 |
| -88.6398 | -88.4576 | -88.2754 | -88.0932 | -87.9109 | -87.7287 | -87.5465 | -87.3642 | -87.1820 | -86.9997 |
| -86.8174 | -86.6351 | -86.4529 | -86.2706 | -86.0882 | -85.9059 | -85.7236 | -85.5413 | -85.3589 | -85.1765 |
| -84.9942 | -84.8118 | -84.6294 | -84.4470 | -84.2646 | -84.0822 | -83.8997 | -83.7173 | -83.5349 | -83.3524 |
| -83.1699 | -82.9875 | -82.8050 | -82.6225 | -82.4400 | -82.2575 | -82.0750 | -81.8924 | -81.7099 | -81.5273 |
| -81.3448 | -81.1622 | -80.9796 | -80.7970 | -80.6144 | -80.4318 | -80.2492 | -80.0666 | -79.8839 | -79.7013 |
| -79.5186 | -79.3360 | -79.1533 | -78.9706 | -78.7879 | -78.6052 | -78.4225 | -78.2398 | -78.0570 | -77.8743 |
| -77.6915 | -77.5088 | -77.3260 | -77.1432 | -76.9604 | -76.7776 | -76.5948 | -76.4120 | -76.2291 | -76.0463 |
| -75.8634 | -75.6806 | -75.4977 | -75.3148 | -75.1320 | -74.9491 | -74.7662 | -74.5832 | -74.4003 | -74.2174 |
| -74.0344 | -73.8515 | -73.6685 | -73.4855 | -73.3025 | -73.1195 | -72.9365 | -72.7535 | -72.5705 | -72.3875 |
| -72.2044 | -72.0213 | -71.8383 | -71.6552 | -71.4721 | -71.2890 | -71.1059 | -70.9228 | -70.7397 | -70.5566 |
| -70.3734 | -70.1903 | -70.0071 | -69.8239 | -69.6407 | -69.4576 | -69.2744 | -69.0911 | -68.9079 | -68.7247 |
| -68.5415 | -68.3582 | -68.1749 | -67.9917 | -67.8084 | -67.6251 | -67.4418 | -67.2585 | -67.0752 | -66.8918 |
| -66.7085 | -66.5251 | -66.3418 | -66.1584 | -65.9751 | -65.7917 | -65.6083 | -65.4249 | -65.2414 | -65.0580 |
| -64.8746 | -64.6911 | -64.5077 | -64.3242 | -64.1407 | -63.9572 | -63.7737 | -63.5902 | -63.4067 | -63.2232 |
| -63.0396 | -62.8561 | -62.6725 | -62.4890 | -62.3054 | -62.1218 | -61.9382 | -61.7546 | -61.5710 | -61.3874 |
| -61.2037 | -61.0201 | -60.8364 | -60.6528 | -60.4691 | -60.2854 | -60.1017 | -59.9180 | -59.7343 | -59.5505 |
| -59.3668 | -59.1831 | -58.9993 | -58.8155 | -58.6318 | -58.4480 | -58.2642 | -58.0804 | -57.8966 | -57.7127 |
| -57.5289 | -57.3451 | -57.1612 | -56.9773 | -56.7935 | -56.6096 | -56.4257 | -56.2418 | -56.0579 | -55.8739 |
| -55.6900 | -55.5060 | -55.3221 | -55.1381 | -54.9541 | -54.7702 | -54.5862 | -54.4022 | -54.2181 | -54.0341 |
| -53.8501 | -53.6660 | -53.4820 | -53.2979 | -53.1138 | -52.9297 | -52.7456 | -52.5615 | -52.3774 | -52.1933 |
| -52.0091 | -51.8250 | -51.6408 | -51.4567 | -51.2725 | -51.0883 | -50.9041 | -50.7199 | -50.5357 | -50.3514 |

FIG. 3c $k_m$ (cont'd)

| | | | | | | | | | |
|---|---|---|---|---|---|---|---|---|---|
| −50.1672 | −49.9830 | −49.7987 | −49.6144 | −49.4301 | −49.2459 | −49.0616 | −48.8772 | −48.6929 | −48.5086 |
| −48.3242 | −48.1399 | −47.9555 | −47.7712 | −47.5868 | −47.4024 | −47.2180 | −47.0336 | −46.8491 | −46.6647 |
| −46.4803 | −46.2958 | −46.1114 | −45.9269 | −45.7424 | −45.5579 | −45.3734 | −45.1889 | −45.0044 | −44.8198 |
| −44.6353 | −44.4507 | −44.2661 | −44.0816 | −43.8970 | −43.7124 | −43.5278 | −43.3432 | −43.1585 | −42.9739 |
| −42.7892 | −42.6046 | −42.4199 | −42.2352 | −42.0506 | −41.8658 | −41.6811 | −41.4964 | −41.3117 | −41.1269 |
| −40.9422 | −40.7574 | −40.5727 | −40.3879 | −40.2031 | −40.0183 | −39.8335 | −39.6486 | −39.4638 | −39.2789 |
| −39.0941 | −38.9092 | −38.7244 | −38.5395 | −38.3546 | −38.1697 | −37.9847 | −37.7998 | −37.6149 | −37.4299 |
| −37.2450 | −37.0600 | −36.8750 | −36.6900 | −36.5050 | −36.3200 | −36.1350 | −35.9500 | −35.7649 | −35.5799 |
| −35.3948 | −35.2097 | −35.0246 | −34.8395 | −34.6544 | −34.4693 | −34.2842 | −34.0990 | −33.9139 | −33.7287 |
| −33.5436 | −33.3584 | −33.1732 | −32.9880 | −32.8028 | −32.6176 | −32.4323 | −32.2471 | −32.0618 | −31.8766 |
| −31.6913 | −31.5060 | −31.3207 | −31.1354 | −30.9501 | −30.7648 | −30.5794 | −30.3941 | −30.2087 | −30.0234 |
| −29.8380 | −29.6526 | −29.4672 | −29.2818 | −29.0964 | −28.9109 | −28.7255 | −28.5400 | −28.3546 | −28.1691 |
| −27.9836 | −27.7981 | −27.6126 | −27.4271 | −27.2416 | −27.0560 | −26.8705 | −26.6849 | −26.4994 | −26.3138 |
| −26.1282 | −25.9426 | −25.7570 | −25.5713 | −25.3857 | −25.2001 | −25.0144 | −24.8287 | −24.6431 | −24.4574 |
| −24.2717 | −24.0860 | −23.9002 | −23.7145 | −23.5288 | −23.3430 | −23.1573 | −22.9715 | −22.7857 | −22.5999 |
| −22.4141 | −22.2283 | −22.0425 | −21.8566 | −21.6708 | −21.4849 | −21.2990 | −21.1132 | −20.9273 | −20.7414 |
| −20.5555 | −20.3695 | −20.1836 | −19.9977 | −19.8117 | −19.6257 | −19.4397 | −19.2538 | −19.0678 | −18.8818 |
| −18.6957 | −18.5097 | −18.3237 | −18.1376 | −17.9515 | −17.7655 | −17.5794 | −17.3933 | −17.2072 | −17.0211 |
| −16.8349 | −16.6488 | −16.4626 | −16.2765 | −16.0903 | −15.9041 | −15.7179 | −15.5317 | −15.3455 | −15.1593 |
| −14.9730 | −14.7868 | −14.6005 | −14.4143 | −14.2280 | −14.0417 | −13.8554 | −13.6691 | −13.4827 | −13.2964 |
| −13.1101 | −12.9237 | −12.7373 | −12.5510 | −12.3646 | −12.1782 | −11.9918 | −11.8053 | −11.6189 | −11.4324 |
| −11.2460 | −11.0595 | −10.8730 | −10.6866 | −10.5001 | −10.3135 | −10.1270 | −9.9405 | −9.7539 | −9.5674 |
| −9.3808 | −9.1942 | −9.0077 | −8.8211 | −8.6344 | −8.4478 | −8.2612 | −8.0745 | −7.8879 | −7.7012 |
| −7.5145 | −7.3279 | −7.1412 | −6.9545 | −6.7677 | −6.5810 | −6.3943 | −6.2075 | −6.0207 | −5.8340 |
| −5.6472 | −5.4604 | −5.2736 | −5.0867 | −4.8999 | −4.7131 | −4.5262 | −4.3393 | −4.1525 | −3.9656 |
| −3.7787 | −3.5918 | −3.4049 | −3.2179 | −3.0310 | −2.8440 | −2.6571 | −2.4701 | −2.2831 | −2.0961 |

FIG. 3d $k_m$ (cont'd)

| | | | | | | | | | |
|---|---|---|---|---|---|---|---|---|---|
| -1.9091 | -1.7221 | -1.5350 | -1.3480 | -1.1609 | -.9739 | -.7868 | -.5997 | -.4126 | -.2255 |
| -.0384 | .1488 | .3359 | .5231 | .7102 | .8974 | 1.0846 | 1.2718 | 1.4590 | 1.6463 |
| 1.8335 | 2.0207 | 2.2080 | 2.3953 | 2.5825 | 2.7698 | 2.9571 | 3.1445 | 3.3318 | 3.5191 |
| 3.7065 | 3.8938 | 4.0812 | 4.2686 | 4.4560 | 4.6434 | 4.8308 | 5.0182 | 5.2057 | 5.3931 |
| 5.5806 | 5.7681 | 5.9555 | 6.1430 | 6.3305 | 6.5181 | 6.7056 | 6.8931 | 7.0807 | 7.2683 |
| 7.4558 | 7.6434 | 7.8310 | 8.0186 | 8.2063 | 8.3939 | 8.5815 | 8.7692 | 8.9569 | 9.1445 |
| 9.3322 | 9.5199 | 9.7076 | 9.8954 | 10.0831 | 10.2708 | 10.4586 | 10.6464 | 10.8342 | 11.0220 |
| 11.2098 | 11.3976 | 11.5854 | 11.7732 | 11.9611 | 12.1490 | 12.3368 | 12.5247 | 12.7126 | 12.9005 |
| 13.0884 | 13.2764 | 13.4643 | 13.6523 | 13.8402 | 14.0282 | 14.2162 | 14.4042 | 14.5922 | 14.7803 |
| 14.9683 | 15.1563 | 15.3444 | 15.5325 | 15.7206 | 15.9087 | 16.0968 | 16.2849 | 16.4730 | 16.6611 |
| 16.8493 | 17.0375 | 17.2256 | 17.4138 | 17.6020 | 17.7903 | 17.9785 | 18.1667 | 18.3549 | 18.5432 |
| 18.7315 | 18.9198 | 19.1081 | 19.2964 | 19.4847 | 19.6730 | 19.8614 | 20.0497 | 20.2381 | 20.4264 |
| 20.6148 | 20.8032 | 29.9916 | 21.1801 | 21.3685 | 21.5569 | 21.7454 | 21.9339 | 22.1224 | 22.3109 |
| 22.4994 | 22.6879 | 22.8764 | 23.0650 | 23.2535 | 23.4421 | 23.6306 | 23.8192 | 24.0078 | 24.1964 |
| 24.3851 | 24.5737 | 24.7624 | 24.9510 | 25.1397 | 25.3284 | 25.5171 | 25.7058 | 25.8945 | 26.0832 |
| 26.2720 | 26.4607 | 26.6495 | 26.8383 | 27.0271 | 27.2159 | 27.4047 | 27.5935 | 27.7823 | 27.9712 |
| 28.1601 | 28.3489 | 28.5378 | 28.7267 | 28.9156 | 29.1045 | 29.2935 | 29.4824 | 29.6714 | 29.8604 |
| 30.0493 | 30.2383 | 30.4273 | 30.6164 | 30.8054 | 30.9944 | 31.1835 | 31.3726 | 31.5616 | 31.7507 |
| 31.9398 | 32.1289 | 32.3181 | 32.5072 | 32.6964 | 32.8855 | 33.0747 | 33.2639 | 33.4531 | 33.6423 |
| 33.8315 | 34.0208 | 34.2100 | 34.3993 | 34.5885 | 34.7778 | 34.9671 | 35.1564 | 35.3458 | 35.5351 |
| 35.7244 | 35.9138 | 36.1032 | 36.2925 | 36.4819 | 36.6713 | 36.8608 | 37.0502 | 37.2396 | 37.4291 |
| 37.6186 | 37.8081 | 37.9975 | 38.1870 | 38.3766 | 38.5661 | 38.7556 | 38.9452 | 39.1348 | 39.3243 |
| 39.5139 | 39.7035 | 39.8931 | 40.0828 | 40.2724 | 40.4621 | 40.6517 | 40.8414 | 41.0311 | 41.2208 |
| 41.4105 | 41.6002 | 41.7900 | 41.9797 | 42.1695 | 42.3593 | 42.5491 | 42.7389 | 42.9287 | 43.1185 |
| 43.3083 | 43.4982 | 43.6881 | 43.8779 | 44.0678 | 44.2577 | 44.4476 | 44.6376 | 44.8275 | 45.0174 |
| 45.2074 | 45.3974 | 45.5874 | 45.7774 | 45.9674 | 46.1574 | 46.3474 | 46.5375 | 46.7276 | 46.9176 |

FIG. 3e $k_m$ (cont'd)

| | | | | | | | | | |
|---|---|---|---|---|---|---|---|---|---|
| 47.1077 | 47.2978 | 47.4879 | 47.6781 | 47.8682 | 48.0583 | 48.2485 | 48.4387 | 48.6289 | 48.8191 |
| 49.0093 | 49.1995 | 49.3898 | 49.5800 | 49.7703 | 49.9605 | 50.1508 | 50.3411 | 50.5315 | 50.7218 |
| 50.9121 | 51.1025 | 51.2928 | 51.4832 | 51.6736 | 51.8640 | 52.0544 | 52.2449 | 52.4353 | 52.6257 |
| 52.8162 | 53.0067 | 53.1972 | 53.3877 | 53.5782 | 53.7687 | 53.9593 | 54.1498 | 54.3404 | 54.5310 |
| 54.7216 | 54.9122 | 55.1028 | 55.2934 | 55.4841 | 55.6748 | 55.8654 | 56.0561 | 56.2468 | 56.4375 |
| 56.6282 | 56.8190 | 57.0097 | 57.2005 | 57.3913 | 57.5820 | 57.7728 | 57.9636 | 58.1545 | 58.3453 |
| 58.5362 | 58.7270 | 58.9179 | 59.1088 | 59.2997 | 59.4906 | 59.6815 | 59.8725 | 60.0634 | 60.2544 |
| 60.4454 | 60.6364 | 60.8274 | 61.0184 | 61.2094 | 61.4005 | 61.5916 | 61.7826 | 61.9737 | 62.1648 |
| 62.3559 | 62.5471 | 62.7382 | 62.9293 | 63.1205 | 63.3117 | 63.5029 | 63.6941 | 63.8853 | 64.0765 |
| 64.2678 | 64.4590 | 64.6503 | 64.8416 | 65.0328 | 65.2242 | 65.4155 | 65.6068 | 65.7982 | 65.9895 |
| 66.1809 | 66.3723 | 66.5637 | 66.7551 | 66.9465 | 67.1380 | 67.3294 | 67.5209 | 67.7123 | 67.9039 |
| 68.0954 | 68.2869 | 68.4784 | 68.6700 | 68.8615 | 69.0531 | 69.2447 | 69.4362 | 69.6279 | 69.8195 |
| 70.0111 | 70.2028 | 70.3945 | 70.5861 | 70.7778 | 70.9695 | 71.1612 | 71.3530 | 71.5447 | 71.7365 |
| 71.9282 | 72.1200 | 72.3118 | 72.5036 | 72.6955 | 72.8873 | 73.0792 | 73.2710 | 73.4629 | 73.6548 |
| 73.8467 | 74.0386 | 74.2306 | 74.4225 | 74.6145 | 74.8064 | 74.9984 | 75.1904 | 75.3824 | 75.5745 |
| 75.7665 | 75.9586 | 76.1506 | 76.3427 | 76.5348 | 76.7269 | 76.9190 | 77.1112 | 77.3033 | 77.4955 |
| 77.6877 | 77.8799 | 78.0721 | 78.2643 | 78.4565 | 78.6488 | 78.8410 | 79.0333 | 79.2256 | 79.4179 |
| 79.6102 | 79.8025 | 79.9949 | 80.1872 | 80.3796 | 80.5720 | 80.7643 | 80.9568 | 81.1492 | 81.3416 |
| 81.5341 | 81.7265 | 81.9190 | 82.1115 | 82.3040 | 82.4965 | 82.6891 | 82.8816 | 83.0742 | 83.2667 |
| 83.4593 | 83.6519 | 83.8446 | 84.0372 | 84.2298 | 84.4225 | 84.6152 | 84.8078 | 85.0005 | 85.1933 |
| 85.3860 | 85.5787 | 85.7715 | 85.9642 | 86.1570 | 86.3498 | 86.5426 | 86.7355 | 86.9283 | 87.1212 |
| 87.3140 | 87.5069 | 87.6998 | 87.8927 | 88.0856 | 88.2786 | 88.4715 | 88.6645 | 88.8575 | 89.0505 |
| 89.2435 | 89.4365 | 89.6295 | 89.8226 | 90.0156 | 90.2087 | 90.4018 | 90.5949 | 90.7880 | 90.9812 |
| 91.1743 | 91.3675 | 91.5606 | 91.7538 | 91.9471 | 92.1403 | 92.3335 | 92.5267 | 92.7200 | 92.9133 |

FIG. 3f $k_m$ (cont'd)

| | | | | | | | | | |
|---|---|---|---|---|---|---|---|---|---|
| 93.1066 | 93.2999 | 93.4932 | 93.6865 | 93.8799 | 94.0732 | 94.2666 | 94.4600 | 94.6534 | 94.8468 |
| 95.0403 | 95.2337 | 95.4272 | 95.6206 | 95.8141 | 96.0076 | 96.2012 | 96.3947 | 96.5882 | 96.7818 |
| 96.9754 | 97.1690 | 97.3626 | 97.5562 | 97.7498 | 97.9435 | 98.1371 | 98.3308 | 98.5245 | 98.7182 |
| 98.9119 | 99.1057 | 99.2994 | 99.4932 | 99.6870 | 99.8808 | 100.0746 | 100.2684 | 100.4622 | 100.6561 |
| 100.8500 | 101.0439 | 101.2378 | 101.4317 | 101.6256 | 101.8195 | 102.0135 | 102.2075 | 102.4014 | 102.5954 |
| 102.7894 | 102.9835 | 103.1775 | 103.3716 | 103.5656 | 103.7597 | 103.9538 | 104.1479 | 104.3421 | 104.5362 |
| 104.7304 | 104.9246 | 105.1188 | 105.3130 | 105.5072 | 105.7014 | 105.8957 | 106.0899 | 106.2842 | 106.4785 |
| 106.6728 | 106.8671 | 107.0615 | 107.2558 | 107.4502 | 107.6446 | 107.8390 | 108.0334 | 108.2278 | 108.4223 |
| 108.6167 | 108.8112 | 109.0057 | 109.2002 | 109.3947 | 109.5892 | 109.7838 | 109.9784 | 110.1729 | 110.3675 |
| 110.5621 | 110.7568 | 110.9514 | 111.1461 | 111.3407 | 111.5354 | 111.7301 | 111.9248 | 112.1195 | 112.3143 |
| 112.5090 | 112.7038 | 112.8986 | 113.0934 | 113.2882 | 113.4831 | 113.6779 | 113.8728 | 114.0677 | 114.2626 |
| 114.4575 | 114.6524 | 114.8474 | 115.0423 | 115.2373 | 115.4323 | 115.6273 | 115.8223 | 116.0173 | 116.2124 |
| 116.4075 | 116.6025 | 116.7976 | 116.9927 | 117.1879 | 117.3830 | 117.5782 | 117.7733 | 117.9685 | 118.1637 |
| 118.3590 | 118.5542 | 118.7494 | 118.9447 | 119.1400 | 119.3353 | 119.5306 | 119.7259 | 119.9213 | 120.1166 |
| 120.3120 | 120.5074 | 120.7028 | 120.8982 | 121.0937 | 121.2891 | 121.4846 | 121.6801 | 121.8756 | 122.0711 |
| 122.2666 | 122.4622 | 122.6577 | 122.8533 | 123.0489 | 123.2445 | 123.4401 | 123.6358 | 123.8314 | 124.0271 |
| 124.2228 | 124.4185 | 124.6142 | 124.8100 | 125.0057 | 125.2015 | 125.3973 | 125.5931 | 125.7889 | 125.9847 |
| 126.1806 | 126.3764 | 126.5723 | 126.7682 | 126.9641 | 127.1601 | 127.3560 | 127.5519 | 127.7479 | 127.9439 |
| 128.1399 | 128.3360 | 128.5320 | 128.7280 | 128.9241 | 129.1202 | 129.3163 | 129.5124 | 129.7086 | 129.9047 |
| 130.1009 | 130.2971 | 130.4933 | 130.6895 | 130.8857 | 131.0820 | 131.2783 | 131.4745 | 131.6709 | 131.8672 |
| 132.0635 | 132.2598 | 132.4562 | 132.6526 | 132.8490 | 133.0454 | 133.2418 | 133.4382 | 133.6347 | 133.8312 |
| 134.0277 | 134.2242 | 134.4207 | 134.6173 | 134.8138 | 135.0104 | 135.2070 | 135.4036 | 135.6003 | 135.7969 |

FIG. 3g $k_m$ (cont'd)

| | | | | | | | | | |
|---|---|---|---|---|---|---|---|---|---|
| 135.9935 | 136.1902 | 136.3869 | 136.5836 | 136.7804 | 136.9771 | 137.1739 | 137.3707 | 137.5674 | 137.7643 |
| 137.9611 | 138.1579 | 138.3548 | 138.5517 | 138.7485 | 138.9455 | 139.1424 | 139.3393 | 139.5363 | 139.7333 |
| 139.9303 | 140.1273 | 140.3243 | 140.5213 | 140.7184 | 140.9155 | 141.1126 | 141.3097 | 141.5068 | 141.7040 |
| 141.9011 | 142.0983 | 142.2955 | 142.4927 | 142.6899 | 142.8872 | 143.0845 | 143.2817 | 143.4790 | 143.6764 |
| 143.8737 | 144.0711 | 144.2684 | 144.4658 | 144.6632 | 144.8606 | 145.0581 | 145.2555 | 145.4530 | 145.6505 |
| 145.8480 | 146.0455 | 146.2431 | 146.4406 | 146.6382 | 146.8358 | 147.0334 | 147.2310 | 147.4287 | 147.6263 |
| 147.8240 | 148.0217 | 148.2194 | 148.4171 | 148.6149 | 148.8127 | 149.0104 | 149.2083 | 149.4061 | 149.6039 |
| 149.8017 | 149.9996 | 150.1975 | 150.3954 | 150.5934 | 150.7913 | 150.9892 | 151.1872 | 151.3852 | 151.5832 |
| 151.7813 | 151.9793 | 152.1774 | 152.3755 | 152.5736 | 152.7717 | 152.9698 | 153.1680 | 153.3662 | 153.5643 |
| 153.7626 | 153.9608 | 154.1590 | 154.3573 | 154.5556 | 154.7539 | 154.9522 | 155.1505 | 155.3489 | 155.5473 |
| 155.7457 | 155.9441 | 156.1425 | 156.3409 | 156.5394 | 156.7379 | 156.9364 | 157.1349 | 157.3334 | 157.5320 |
| 157.7305 | 157.9291 | 158.1277 | 158.3264 | 158.5250 | 158.7237 | 158.9224 | 159.1210 | 159.3198 | 159.5185 |
| 159.7173 | 159.9160 | 160.1148 | 160.3136 | 160.5125 | 160.7113 | 160.9102 | 161.1091 | 161.3080 | 161.5069 |
| 161.7059 | 161.9048 | 162.1038 | 162.3028 | 162.5018 | 162.7008 | 162.8999 | 163.0990 | 163.2980 | 163.4971 |
| 163.6963 | 163.8954 | 164.0946 | 164.2938 | 164.4930 | 164.6922 | 164.8915 | 165.0907 | 165.2900 | 165.4893 |
| 165.6886 | 165.8880 | 166.0873 | 166.2867 | 166.4861 | 166.6855 | 166.8849 | 167.0844 | 167.2838 | 167.4833 |
| 167.6829 | 167.8824 | 168.0819 | 168.2815 | 168.4811 | 168.6807 | 168.8803 | 169.0800 | 169.2796 | 169.4793 |
| 169.6790 | 169.8788 | 170.0785 | 170.2783 | 170.4780 | 170.6779 | 170.8777 | 171.0775 | 171.2774 | 171.4773 |
| 171.6772 | 171.8771 | 172.0770 | 172.2770 | 172.4770 | 172.6770 | 172.8770 | 173.0770 | 173.2771 | 173.4772 |
| 173.6773 | 173.8774 | 174.0775 | 174.2777 | 174.4779 | 174.6781 | 174.8783 | 175.0785 | 175.2788 | 175.4791 |
| 175.6794 | 175.8797 | 176.0801 | 176.2804 | 176.4808 | 176.6812 | 176.8816 | 177.0821 | 177.2825 | 177.4830 |
| 177.6835 | 177.8841 | 178.0846 | 178.2852 | 178.4858 | 178.6864 | 178.8870 | 179.0877 | 179.2883 | 179.4890 |
| 179.6897 | 179.8905 | 180.0912 | 180.2920 | 180.4928 | 180.6936 | 180.8945 | 181.0954 | 181.2962 | 181.4971 |
| 181.6981 | 181.8990 | 182.1000 | 182.3010 | 182.5020 | 182.7030 | 182.9041 | 183.1051 | 183.3062 | 183.5074 |
| 183.7085 | 183.9097 | 184.1109 | 184.3121 | 184.5133 | 184.7145 | 184.9158 | 185.1171 | 185.3184 | 185.5198 |
| 185.7211 | 185.9225 | 186.1239 | 186.3253 | 186.5268 | 186.7282 | 186.9297 | 187.1313 | 187.3328 | 187.5343 |
| 187.7359 | 187.9375 | 188.1392 | 188.3408 | 188.5425 | 188.7442 | 188.9459 | 189.1476 | 189.3494 | 189.5512 |
| 189.7530 | 189.9548 | 190.1567 | 190.3586 | 190.5605 | 190.7624 | 190.9643 | 191.1663 | 191.3683 | 191.5703 |
| 191.7724 | | | | | | | | | |

FIG. 3h $h_m$

| | | | | | | | | | |
|---|---|---|---|---|---|---|---|---|---|
| −355.0659 | −354.7434 | −354.4209 | −354.0984 | −353.7758 | −353.4531 | −353.1305 | −352.8078 | −352.4850 | −352.1623 |
| −351.8394 | −351.5166 | −351.1937 | −350.8708 | −350.5478 | −350.2248 | −349.9018 | −349.5787 | −349.2556 | −348.9325 |
| −348.6093 | −348.2861 | −347.9629 | −347.6396 | −347.3162 | −346.9929 | −346.6695 | −346.3460 | −346.0226 | −345.6991 |
| −345.3755 | −345.0520 | −344.7284 | −344.4047 | −344.0810 | −343.7573 | −343.4335 | −343.1097 | −342.7859 | −342.4620 |
| −342.1381 | −341.8141 | −341.4901 | −341.1661 | −340.8421 | −340.5180 | −340.1939 | −339.8697 | −339.5455 | −339.2213 |
| −338.8970 | −338.5727 | −338.2483 | −337.9239 | −337.5995 | −337.2750 | −336.9505 | −336.6260 | −336.3014 | −335.9768 |
| −335.6521 | −335.3275 | −335.0027 | −334.6779 | −334.3532 | −334.0283 | −333.7034 | −333.3785 | −333.0536 | −332.7286 |
| −332.4036 | −332.0785 | −331.7534 | −331.4283 | −331.1031 | −330.7779 | −330.4526 | −330.1273 | −329.8020 | −329.4767 |
| −329.1513 | −328.8258 | −328.5004 | −328.1749 | −327.8493 | −327.5237 | −327.1981 | −326.8725 | −326.5468 | −326.2210 |
| −325.8953 | −325.5694 | −325.2436 | −324.9177 | −324.5918 | −324.2658 | −323.9398 | −323.613[illegible] | −323.2877 | −322.9616 |
| −322.6354 | −322.3093 | −321.9830 | −321.6568 | −321.3304 | −321.0041 | −320.6777 | −320.3513 | −320.0248 | −319.6984 |
| −319.3719 | −319.0453 | −318.7186 | −318.3920 | −318.0653 | −317.7386 | −317.4119 | −317.0851 | −316.7582 | −316.4314 |
| −316.1045 | −315.7775 | −315.4505 | −315.1235 | −314.7964 | −314.4693 | −314.1422 | −313.8150 | −313.4878 | −313.1606 |
| −312.8333 | −312.5059 | −312.1786 | −311.8511 | −311.5237 | −311.1962 | −310.8687 | −310.5411 | −310.2135 | −309.8859 |
| −309.5582 | −309.2305 | −308.9027 | −308.5750 | −308.2471 | −307.9192 | −307.5913 | −307.2634 | −306.9354 | −306.6074 |
| −306.2793 | −305.9512 | −305.6230 | −305.2949 | −304.9666 | −304.6384 | −304.3101 | −303.9818 | −303.6534 | −303.3250 |
| −302.9966 | −302.6681 | −302.3395 | −302.0110 | −301.6823 | −301.3537 | −301.0250 | −300.6963 | −300.3675 | −300.0387 |
| −299.7099 | −299.3810 | −299.0521 | −298.7231 | −298.3941 | −298.0651 | −297.7361 | −297.4069 | −297.0778 | −296.7486 |
| −296.4193 | −296.0901 | −295.7607 | −295.4314 | −295.1020 | −294.7726 | −294.4431 | −294.1136 | −293.7841 | −293.4545 |
| −293.1248 | −292.7952 | −292.4655 | −292.1357 | −291.8059 | −291.4761 | −291.1462 | −290.8164 | −290.4864 | −290.1565 |
| −289.8264 | −289.4963 | −289.1663 | −288.8361 | −288.5060 | −288.1757 | −287.8455 | −287.5152 | −287.1848 | −286.8544 |
| −286.5240 | −286.1936 | −285.8631 | 285.5326 | −285.2020 | −284.8714 | −284.5407 | −284.2100 | −283.8793 | −283.5485 |
| −283.2177 | −282.8868 | −282.5560 | −282.2250 | −281.8940 | −281.5630 | −281.2320 | −280.9009 | −280.5697 | −280.2385 |
| −279.9073 | −279.5760 | −279.2448 | −278.9135 | −278.5821 | −278.2507 | −277.9192 | −277.5877 | −277.2562 | −276.9246 |

FIG. 4a $h_m$ (cont'd)

| | | | | | | | | | |
|---|---|---|---|---|---|---|---|---|---|
| -276.5930 | -276.2613 | -275.9296 | -275.5979 | -275.2661 | -274.9343 | -274.6024 | -274.2705 | -273.9386 | -273.6066 |
| -273.2746 | -272.9425 | -272.6104 | -272.2783 | -271.9461 | -271.6139 | -271.2816 | -270.9493 | -270.6169 | -270.2846 |
| -269.9521 | -269.6196 | -269.2871 | -268.9546 | -268.6220 | -268.2894 | -267.9567 | -267.6240 | -267.2913 | -266.9584 |
| -266.6256 | -266.2927 | -265.9598 | -265.6269 | -265.2938 | -264.9608 | -264.6277 | -264.2946 | -263.9614 | -263.6282 |
| -263.2950 | -262.9617 | -262.6284 | -262.2950 | -261.9616 | -261.6281 | -261.2946 | -260.9611 | -260.6275 | -260.2939 |
| -259.9602 | -259.6265 | -259.2928 | -258.9590 | -258.6252 | -258.2913 | -257.9574 | -257.6235 | -257.2895 | -256.9554 |
| -256.6214 | -256.2873 | -255.9531 | -255.6189 | -255.2847 | -254.9504 | -254.6161 | -254.2817 | -253.9473 | -253.6128 |
| -253.2784 | -252.9438 | -252.6093 | -252.2746 | -251.9400 | -251.6053 | -251.2705 | -250.9358 | -250.6010 | -250.2661 |
| -249.9312 | -249.5962 | -249.2612 | -248.9262 | -248.5911 | -248.2560 | -247.9208 | -247.5856 | -247.2504 | -246.9151 |
| -246.5798 | -246.2444 | -245.9090 | -245.5736 | -245.2381 | -244.9025 | -244.5670 | -244.2313 | -243.8957 | -243.5600 |
| -243.2242 | -242.8884 | -242.5526 | -242.2167 | -241.8808 | -241.5448 | -241.2088 | -240.8728 | -240.5367 | -240.2006 |
| -239.8644 | -239.5282 | -239.1919 | -238.8557 | -238.5193 | -238.1829 | -237.8465 | -237.5100 | -237.1735 | -236.8369 |
| -236.5003 | -236.1637 | -235.8270 | -235.4903 | -235.1535 | -234.8167 | -234.4799 | -234.1429 | -233.8060 | -233.4690 |
| -233.1320 | -232.7949 | -232.4578 | -232.1207 | -231.7835 | -231.4462 | -231.1089 | -230.7716 | -230.4342 | -230.0968 |
| -229.7594 | -229.4218 | -229.0843 | -229.7467 | -228.4091 | -228.0714 | -227.7337 | -227.3959 | -227.0581 | -226.7203 |
| -226.3824 | -226.0445 | -225.7065 | -225.3685 | -225.0304 | -224.6923 | -224.3541 | -224.0159 | -223.6777 | -223.3394 |
| -223.0011 | -222.6627 | -222.3243 | -221.9859 | -221.6474 | -221.3088 | -220.9702 | -220.6316 | -220.2929 | -219.9542 |
| -219.6154 | -219.2766 | -218.9378 | -218.5989 | -218.2599 | -217.9210 | -217.5819 | -217.2429 | -216.9037 | -216.5646 |
| -216.2254 | -215.8861 | -215.5469 | -215.2075 | -214.8681 | -214.5287 | -214.1893 | -213.8497 | -213.5102 | -213.1706 |
| -212.8309 | -212.4913 | -212.1515 | -211.8118 | -211.4719 | -211.1321 | -210.7922 | -210.4522 | -210.1122 | -209.7722 |
| -209.4321 | -209.0919 | -208.7518 | -208.4115 | -208.0713 | -207.7310 | -207.3906 | -207.0502 | -206.7098 | -206.3693 |
| -206.0287 | -205.6882 | -205.3475 | -205.0069 | -204.6662 | -204.3254 | -203.9846 | -203.6437 | -203.3028 | -202.9619 |
| -202.6209 | 202.2799 | -201.9388 | -201.5977 | -201.2565 | -200.9153 | -200.5741 | -200.2328 | -199.8914 | -199.5500 |
| -199.2086 | -198.8671 | -198.5256 | -198.1841 | -197.8424 | -197.5008 | -197.1591 | -196.8173 | -196.4755 | -196.1337 |
| -195.7918 | -195.4499 | -195.1079 | -194.7659 | -194.4238 | -194.0817 | -193.7395 | -193.3973 | -193.0551 | -192.7128 |
| -192.3704 | -192.0280 | -191.6856 | -191.3431 | -191.0006 | -190.6580 | -190.3154 | -189.9727 | -189.6300 | -189.2873 |

FIG. 4b $h_m$ (cont'd)

| | | | | | | | | | |
|---|---|---|---|---|---|---|---|---|---|
| −188.9445 | −188.6016 | −188.2588 | −187.9158 | −187.5728 | −187.2298 | −186.8867 | −186.5436 | −186.2004 | −185.8572 |
| −185.5139 | −165.1707 | −184.8273 | −184.4839 | −184.1404 | −183.7970 | −183.4534 | −183.1098 | −182.7662 | −182.4225 |
| −182.0788 | −181.7350 | −181.3912 | −181.0473 | −180.7034 | −180.3595 | −180.0155 | −179.6714 | −179.3273 | −178.9832 |
| −178.6390 | −178.2948 | −177.9505 | −177.6062 | −177.2618 | −176.9173 | −176.5729 | −176.2284 | −175.8838 | 175.5392 |
| −175.1945 | −174.8498 | −174.5051 | −174.1603 | −173.8154 | −173.4705 | −173.1256 | −172.7806 | −172.4356 | −172.0905 |
| −171.7454 | −171.4002 | −171.0550 | −170.7097 | −170.3644 | −170.0190 | −169.6736 | −169.3282 | −168.9826 | −168.6371 |
| −168.2915 | −167.9458 | −167.6002 | −167.2544 | −166.9086 | −166.5628 | −166.2169 | −165.8710 | −165.5250 | −165.1789 |
| −164.8329 | −164.4867 | −164.1405 | −163.7943 | −163.4481 | −163.1018 | −162.7554 | −162.4090 | −162.0625 | −161.7160 |
| −161.3695 | −161.0229 | −160.6762 | −160.3295 | −159.9828 | −159.6360 | −159.2891 | −158.9422 | −158.5953 | −158.2483 |
| −157.9013 | −157.5542 | −157.2070 | −156.8599 | −156.5126 | −156.1653 | −155.8180 | −155.4706 | −155.1232 | −154.7758 |
| −154.4282 | −154.0807 | −153.7330 | −153.3854 | −153.0377 | −152.6899 | −152.3421 | −151.9942 | −151.6463 | −151.2983 |
| −150.9503 | −150.6023 | −150.2542 | −149.9060 | −149.5578 | −149.2096 | −148.8613 | −148.5129 | −148.1645 | −147.8161 |
| −147.4676 | −147.1190 | −146.7704 | −146.4218 | −146.0731 | −145.7243 | −145.3756 | −145.0267 | −144.6778 | −144.3289 |
| −143.9799 | −143.6309 | −143.2818 | −142.9326 | −142.5835 | −142.2342 | −141.8849 | −141.5356 | −141.1862 | −140.8368 |
| −140.4873 | −140.1378 | −139.7882 | −139.4385 | −139.0889 | −138.7391 | −138.3893 | −138.0395 | −137.6896 | −137.3397 |
| −136.9897 | −136.6397 | −136.2896 | −135.9395 | −135.5893 | −135.2391 | −134.8888 | −134.5385 | −134.1881 | −133.8377 |
| −133.4872 | −133.1366 | −132.7861 | −132.4354 | −132.0847 | −131.7340 | −131.3832 | −131.0324 | −130.6815 | −130.3305 |
| −129.9796 | −129.6285 | −129.2774 | −128.9263 | −128.5751 | −128.2239 | −127.8726 | −127.5212 | −127.1699 | −126.8184 |
| −126.4669 | −126.1154 | −125.7638 | −125.4121 | −125.0604 | −124.7087 | −124.3569 | −124.0051 | −123.6531 | −123.3012 |
| −122.9492 | −122.5971 | −122.2450 | −121.8929 | −121.5407 | −121.1884 | −120.8361 | −120.4837 | −120.1313 | −119.7789 |
| −119.4264 | −119.0738 | −118.7212 | −118.3685 | −118.0158 | −117.6630 | −117.3102 | −116.9573 | −116.6044 | −116.2514 |
| −115.8984 | −115.5453 | −115.1922 | −114.8390 | −114.4857 | −114.1325 | −113.7791 | −113.4257 | −113.0723 | −112.7188 |
| −112.3652 | −112.0116 | −111.6580 | −111.3043 | −110.9505 | −110.5967 | −110.2428 | −109.8889 | −109.5350 | −109.1809 |

FIG. 4c $h_m$ (cont'd)

| | | | | | | | | | |
|---|---|---|---|---|---|---|---|---|---|
| -108.8269 | -108.4727 | -108.1186 | -107.7643 | -107.4100 | -107.0557 | -106.7013 | -106.3469 | -105.9924 | -105.6378 |
| -105.2833 | -104.9286 | -104.5739 | -104.2192 | -103.8643 | -103.5095 | -103.1546 | -102.7996 | -102.4446 | -102.0895 |
| -101.7344 | -101.3792 | -101.0240 | -100.6687 | -100.3134 | -99.9580 | -99.6025 | -99.2470 | -98.8915 | -98.5359 |
| -98.1802 | -97.8245 | -97.4687 | -97.1129 | -96.7571 | -96.4011 | -96.0452 | -95.6891 | -95.3330 | -94.9769 |
| -94.6207 | -94.2645 | -93.9082 | -93.5518 | -93.1954 | -92.8390 | -92.4824 | -92.1259 | -91.7693 | -91.4126 |
| -91.0559 | -90.6991 | -90.3422 | -89.9853 | -89.6284 | -89.2714 | -88.9143 | -88.5572 | -88.2001 | -87.8428 |
| -87.4856 | -87.1282 | -86.7709 | -86.4134 | -86.0559 | -85.6984 | -85.3408 | -84.9832 | -84.6255 | -84.2677 |
| -83.9099 | -83.5520 | -83.1941 | -82.8361 | -82.4780 | -82.1200 | -81.7618 | -81.4036 | -81.0453 | -80.6870 |
| -80.3287 | -79.9703 | -79.6118 | -79.2533 | -78.8947 | -78.5360 | -78.1773 | -77.8186 | -77.4598 | -77.1009 |
| -76.7420 | -76.3830 | -76.0240 | -75.6649 | -75.3058 | -74.9466 | -74.5873 | -74.2280 | -73.8687 | -73.5092 |
| -73.1498 | -72.7903 | -72.4306 | -72.0710 | -71.7113 | -71.3516 | -70.9917 | -70.6319 | -70.2720 | -69.9120 |
| -69.5520 | -69.1919 | -68.8317 | -68.4715 | -68.1113 | -67.7509 | -67.3906 | -67.0302 | -66.6697 | -66.3091 |
| -65.9485 | -65.5879 | -65.2272 | -64.8664 | -64.5056 | -64.1447 | -63.7838 | -63.4228 | -63.0618 | -62.7006 |
| -62.3395 | -61.9783 | -61.6170 | -61.2557 | -60.8943 | -60.5328 | -60.1713 | -59.8098 | -59.4481 | -59.0865 |
| -58.7247 | -58.3629 | -58.0011 | -57.6392 | -57.2772 | -56.9152 | -56.5531 | -56.1910 | -55.8288 | -55.4666 |
| -55.1043 | -54.7419 | -54.3795 | -54.0170 | -53.6544 | -53.2919 | -52.9292 | -52.5665 | -52.2037 | -51.8409 |
| -51.4780 | -51.1151 | -50.7521 | -50.3890 | -50.0259 | -49.6627 | -49.2995 | -48.9362 | -48.5728 | -48.2094 |
| -47.8460 | -47.4824 | -47.1189 | -46.7552 | -46.3915 | -46.0278 | -45.6639 | -45.3001 | -44.9361 | -44.5721 |
| -44.2081 | -43.8440 | -43.4798 | -43.1156 | -42.7513 | -42.3869 | -42.0225 | -41.6581 | -41.2935 | -40.9289 |
| -40.5643 | -40.1996 | -39.8349 | -39.4700 | -39.1051 | -38.7402 | -38.3752 | -38.0102 | -37.6451 | -37.2799 |
| -36.9146 | -36.5493 | -36.1840 | -35.8186 | -35.4531 | -35.0875 | -34.7220 | -34.3563 | -33.9906 | -33.6248 |
| -33.2590 | -32.8931 | -32.5271 | -32.1611 | -31.7950 | -31.4289 | -31.0627 | -30.6964 | -30.3301 | -29.9638 |
| -29.5973 | -29.2308 | -28.8643 | -28.4976 | -28.1310 | -27.7642 | -27.3974 | -27.0306 | -26.6636 | -26.2967 |
| -25.9296 | -25.5625 | -25.1953 | -24.8281 | -24.4608 | -24.0935 | -23.7261 | -23.3586 | -22.9911 | -22.6235 |
| -22.2558 | -21.8881 | -21.5203 | -21.1525 | -20.7846 | -20.4166 | -20.0486 | -19.6805 | -19.3124 | -18.9442 |
| -18.5759 | -18.2075 | -17.8392 | -17.4707 | -17.1022 | -16.7336 | -16.3650 | -15.9963 | -15.6275 | -15.2586 |
| -14.8898 | -14.5208 | -14.1518 | -13.7827 | -13.4136 | -13.04444 | -12.6751 | -12.3058 | -11.9364 | -11.5669 |

FIG. 4d $h_m$ (cont'd)

| | | | | | | | | | |
|---|---|---|---|---|---|---|---|---|---|
| −11.1974 | −10.8279 | −10.4582 | −10.0885 | −9.7187 | −9.3489 | −8.9790 | −8.6091 | −8.2390 | −7.8690 |
| −7.4988 | −7.1286 | −6.7583 | −6.3880 | −6.0176 | −5.6472 | −5.2766 | −4.9060 | −4.5354 | −4.1647 |
| −3.7939 | −3.4230 | −3.0521 | −2.6812 | −2.3101 | −1.9391 | −1.5679 | −1.1967 | −.8254 | −.4540 |
| −.0826 | .2889 | .6604 | 1.0320 | 1.4037 | 1.7754 | 2.1472 | 2.5191 | 2.8910 | 3.2630 |
| 3.6351 | 4.0072 | 4.3794 | 4.7516 | 5.1240 | 5.4964 | 5.8688 | 6.2413 | 6.6139 | 6.9865 |
| 7.3592 | 7.7320 | 8.1049 | 8.4777 | 8.8507 | 9.2238 | 9.5969 | 9.9700 | 10.3433 | 10.7166 |
| 11.0899 | 11.4633 | 11.8368 | 12.2104 | 12.5840 | 12.9577 | 13.3314 | 13.7053 | 14.0792 | 14.4531 |
| 14.8271 | 15.2012 | 15.5754 | 15.9496 | 16.3239 | 16.6982 | 17.0726 | 17.4471 | 17.8217 | 18.1963 |
| 18.5710 | 18.9457 | 19.3205 | 19.6954 | 20.0703 | 20.4454 | 20.8205 | 21.1956 | 21.5708 | 21.9461 |
| 22.3214 | 22.6969 | 23.0724 | 23.4479 | 23.8235 | 24.1992 | 24.5750 | 24.9508 | 25.3267 | 25.7026 |
| 26.0787 | 26.4547 | 26.8309 | 27.2071 | 27.5834 | 27.9598 | 28.3362 | 28.7127 | 29.0893 | 29.4659 |
| 29.8426 | 30.2194 | 30.5962 | 30.9731 | 31.3501 | 31.7272 | 32.1043 | 32.4814 | 32.8587 | 33.2360 |
| 33.6134 | 33.9909 | 34.3684 | 34.7460 | 35.1236 | 35.5014 | 35.8792 | 36.2570 | 36.6350 | 37.0130 |
| 37.3911 | 37.7692 | 38.1474 | 38.5257 | 38.9041 | 39.2825 | 39.6610 | 40.0396 | 40.4182 | 40.7969 |
| 41.1757 | 41.5545 | 41.9334 | 42.3124 | 42.6915 | 43.0706 | 43.4498 | 43.8290 | 44.2084 | 44.5878 |
| 44.9672 | 45.3468 | 45.7264 | 46.1061 | 46.4858 | 46.8657 | 47.2456 | 47.6256 | 48.0056 | 48.3857 |
| 48.7659 | 49.1461 | 49.5265 | 49.9069 | 50.2873 | 50.6679 | 51.0485 | 51.4291 | 51.8099 | 52.1907 |
| 52.5716 | 52.9526 | 53.3336 | 53.7147 | 54.0959 | 54.4772 | 54.8585 | 55.2399 | 55.6214 | 56.0029 |
| 56.3845 | 56.7662 | 57.1480 | 57.5298 | 57.9117 | 58.2937 | 58.6757 | 59.0579 | 59.4401 | 59.8223 |
| 60.2047 | 60.5871 | 60.9696 | 61.3521 | 61.7348 | 62.1175 | 62.5002 | 62.8831 | 63.2660 | 63.6490 |
| 64.0321 | 64.4152 | 64.7985 | 65.1818 | 65.5651 | 65.9486 | 66.3321 | 66.7157 | 67.0993 | 67.4831 |
| 67.8669 | 68.2508 | 68.6347 | 69.0188 | 69.4029 | 69.7870 | 70.1713 | 70.5556 | 70.9400 | 71.3245 |
| 71.7091 | 72.0937 | 72.4784 | 72.8632 | 73.2480 | 73.6330 | 74.0180 | 74.4031 | 74.7882 | 75.1734 |

FIG. 4e $h_m$ (cont'd)

| | | | | | | | | | |
|---|---|---|---|---|---|---|---|---|---|
| 75.5588 | 75.9441 | 76.3296 | 76.7151 | 77.1007 | 77.4864 | 77.8722 | 78.2580 | 78.6439 | 79.0299 |
| 79.4160 | 79.8021 | 80.1883 | 80.5746 | 80.9610 | 81.3475 | 81.7340 | 82.1206 | 82.5073 | 82.8940 |
| 83.2808 | 83.6677 | 84.0547 | 84.4418 | 84.8289 | 85.2161 | 85.6034 | 85.9908 | 86.3783 | 86.7658 |
| 87.1534 | 87.5411 | 87.9288 | 88.3167 | 88.7046 | 89.0926 | 89.4806 | 89.8688 | 90.2570 | 90.6453 |
| 91.0337 | 91.4221 | 91.8107 | 92.1993 | 92.5880 | 92.9768 | 93.3656 | 93.7546 | 94.1436 | 94.5326 |
| 94.9218 | 95.3111 | 95.7004 | 96.0898 | 96.4793 | 96.8689 | 97.2585 | 97.6482 | 98.0380 | 98.4279 |
| 98.8179 | 99.2079 | 99.5980 | 99.9882 | 100.3785 | 100.7689 | 101.1593 | 101.5498 | 101.9404 | 102.3311 |
| 102.7219 | 103.1127 | 103.5036 | 103.8946 | 104.2857 | 104.6769 | 105.0681 | 105.4595 | 105.8509 | 106.2424 |
| 106.6339 | 107.0256 | 107.4173 | 107.8092 | 108.2010 | 108.5930 | 108.9851 | 109.3772 | 109.7695 | 110.1618 |
| 110.5542 | 110.9466 | 111.3392 | 111.7318 | 112.1245 | 112.5173 | 112.9102 | 113.3032 | 113.6963 | 114.0894 |
| 114.4826 | 114.8759 | 115.2693 | 115.6627 | 116.0563 | 116.4499 | 116.8436 | 117.2374 | 117.6313 | 118.0253 |
| 118.4193 | 118.8135 | 119.2077 | 119.6020 | 119.9963 | 120.3908 | 120.7854 | 121.1800 | 121.5747 | 121.9695 |
| 122.3644 | 122.7594 | 123.1545 | 123.5496 | 123.9448 | 124.3402 | 124.7356 | 125.1310 | 125.5266 | 125.9223 |
| 126.3180 | 126.7139 | 127.1097 | 127.5058 | 127.9019 | 128.2980 | 128.6943 | 129.0906 | 129.4870 | 129.8836 |
| 130.2802 | 130.6768 | 131.0736 | 131.4705 | 131.8674 | 132.2645 | 132.6616 | 133.0588 | 133.4561 | 133.8535 |
| 134.2509 | 134.6485 | 135.0462 | 135.4439 | 135.8417 | 136.2396 | 136.6376 | 137.0357 | 137.4339 | 137.8321 |
| 138.2305 | 138.6289 | 139.0275 | 139.4261 | 139.8248 | 140.2235 | 140.6224 | 141.0214 | 141.4205 | 141.8196 |
| 142.2188 | 142.6182 | 143.0176 | 143.4171 | 143.8167 | 144.2163 | 144.6161 | 145.0160 | 145.4159 | 145.8160 |
| 146.2161 | 146.6163 | 147.0167 | 147.4171 | 147.8175 | 148.2182 | 148.6188 | 149.0196 | 149.4204 | 149.8214 |
| 150.2224 | 150.6236 | 151.0248 | 151.4261 | 151.8275 | 152.2290 | 152.6306 | 153.0323 | 153.4340 | 153.8359 |
| 154.2379 | 154.6399 | 155.0420 | 155.4443 | 155.8566 | 156.2490 | 156.6515 | 157.0541 | 157.4569 | 157.8596 |
| 158.2625 | 158.6655 | 159.0686 | 159.4718 | 159.8750 | 160.2784 | 160.6818 | 161.0853 | 161.4890 | 161.8927 |
| 162.2965 | 162.7004 | 163.1044 | 163.5085 | 163.9128 | 164.3170 | 164.7214 | 165.1259 | 165.5305 | 165.9352 |
| 166.3400 | 166.7448 | 167.1498 | 167.5548 | 167.9600 | 168.3652 | 168.7706 | 169.1760 | 169.5816 | 169.9872 |
| 170.3929 | 170.7988 | 171.2047 | 171.6107 | 172.0168 | 172.4230 | 172.8294 | 173.2358 | 173.6423 | 174.0489 |
| 174.4556 | 174.8624 | 175.2693 | 175.6763 | 176.0834 | 176.4906 | 176.8979 | 177.3052 | 177.7127 | 178.1203 |
| 178.5280 | 178.9358 | 179.3437 | 179.7517 | 180.1598 | 180.5679 | 180.9762 | 181.3846 | 181.7931 | 182.2017 |

FIG. 4f $h_m$ (cont'd)

| | | | | | | | | | |
|---|---|---|---|---|---|---|---|---|---|
| 182.6104 | 183.0191 | 183.4280 | 183.8370 | 184.2461 | 184.6553 | 185.0646 | 185.4739 | 185.8834 | 186.2930 |
| 186.7027 | 187.1125 | 187.5224 | 187.9324 | 188.3425 | 188.7527 | 189.1630 | 189.5734 | 189.9839 | 190.3945 |
| 190.8052 | 191.2160 | 191.6270 | 192.0380 | 192.4491 | 192.8603 | 193.2717 | 193.6831 | 194.0946 | 194.5063 |
| 194.9180 | 195.3299 | 195.7418 | 196.1539 | 196.5660 | 196.9783 | 197.3907 | 197.8032 | 198.2158 | 198.6284 |
| 199.0412 | 199.4541 | 199.8672 | 200.2802 | 200.6935 | 201.1068 | 201.5202 | 201.9338 | 202.3474 | 202.7612 |
| 203.1750 | 203.5890 | 204.0031 | 204.4172 | 204.8315 | 205.2459 | 205.6604 | 206.0750 | 206.4897 | 206.9045 |
| 207.3195 | 207.7345 | 208.1497 | 208.5649 | 208.9803 | 209.3958 | 209.8114 | 210.2271 | 210.6429 | 211.0588 |
| 211.4748 | 211.8909 | 212.3072 | 212.7236 | 213.1400 | 213.5566 | 213.9733 | 214.3901 | 214.8070 | 215.2240 |
| 215.6411 | 216.0584 | 216.4757 | 216.8932 | 217.3108 | 217.7285 | 218.1463 | 218.5642 | 218.9822 | 219.4004 |
| 219.8186 | 220.2370 | 220.6555 | 221.0741 | 221.4928 | 221.9116 | 222.3305 | 222.7496 | 223.1687 | 223.5880 |
| 224.0074 | 224.4269 | 224.8465 | 225.2663 | 225.6861 | 226.1061 | 226.5262 | 226.9464 | 227.3667 | 227.7871 |
| 228.2077 | 228.6284 | 229.0491 | 229.4700 | 229.8910 | 230.3122 | 230.7334 | 231.1548 | 231.5763 | 231.9979 |
| 232.4196 | 232.8415 | 233.2634 | 233.6855 | 234.1077 | 234.5300 | 234.9524 | 235.3750 | 235.7976 | 236.2205 |
| 236.6434 | 237.0664 | 237.4895 | 237.9128 | 238.3362 | 238.7597 | 239.1834 | 239.6071 | 240.0310 | 240.4550 |
| 240.8791 | 241.3034 | 241.7277 | 242.1522 | 242.5769 | 243.0016 | 243.4264 | 243.8514 | 244.2765 | 244.7018 |
| 245.1271 | 245.5526 | 245.9782 | 246.4039 | 246.8298 | 247.2557 | 247.6818 | 248.1081 | 248.5344 | 248.9609 |
| 249.3875 | 249.8142 | 250.2411 | 250.6681 | 251.0952 | 251.5224 | 251.9498 | 252.3773 | 252.8049 | 253.2326 |
| 253.6605 | 254.0885 | 254.5166 | 254.9449 | 255.3733 | 255.8018 | 256.2305 | 256.6592 | 257.0881 | 257.5172 |
| 257.9464 | 258.3756 | 258.8051 | 259.2346 | 259.6643 | 260.0941 | 260.5241 | 260.9542 | 261.3844 | 261.8148 |
| 262.2452 | 262.6758 | 263.1066 | 263.5375 | 263.9685 | 264.3997 | 264.8309 | 265.2623 | 265.6939 | 266.1256 |
| 266.5574 | 266.9893 | 267.4214 | 267.8537 | 268.2860 | 268.7185 | 269.1512 | 269.5840 | 270.0169 | 270.4500 |
| 270.8831 | 271.3164 | 271.7499 | 272.1835 | 272.6172 | 273.0511 | 273.4851 | 273.9193 | 274.3536 | 274.7881 |
| 275.2226 | 275.6573 | 276.0922 | 276.5272 | 276.9623 | 277.3976 | 277.8330 | 278.2686 | 278.7043 | 279.1402 |

FIG. 4g $h_m$ (cont'd)

| | | | | | | | | | |
|---|---|---|---|---|---|---|---|---|---|
| 279.5761 | 280.0123 | 280.4486 | 280.8850 | 281.3216 | 281.7583 | 282.1952 | 282.6321 | 283.0693 | 283.5066 |
| 283.9440 | 284.3816 | 284.8194 | 285.2572 | 285.6953 | 286.1335 | 286.5717 | 287.0102 | 287.4489 | 287.8876 |
| 288.3265 | 288.7656 | 289.2048 | 289.6442 | 290.0837 | 290.5234 | 290.9631 | 291.4031 | 291.8432 | 292.2835 |
| 292.7240 | 293.1645 | 293.6053 | 294.0461 | 294.4872 | 294.9284 | 295.3697 | 295.8112 | 296.2529 | 296.6946 |
| 297.1366 | 297.5787 | 298.0210 | 298.4634 | 298.9060 | 299.3488 | 299.7917 | 300.2347 | 300.6780 | 301.1213 |
| 301.5649 | 302.0086 | 302.4524 | 302.8965 | 303.3406 | 303.7850 | 304.2294 | 304.6741 | 305.1190 | 305.5639 |
| 306.0091 | 306.4543 | 306.8998 | 307.3455 | 307.7913 | 308.2372 | 308.6834 | 309.1297 | 309.5761 | 310.0228 |
| 310.4696 | 310.9166 | 311.3637 | 311.8110 | 312.2585 | 312.7061 | 313.1539 | 313.6019 | 314.0500 | 314.4983 |
| 314.9469 | 315.3955 | 315.8443 | 316.2933 | 316.7425 | 317.1919 | 317.6414 | 318.0911 | 318.5410 | 318.9910 |
| 319.4413 | 319.8917 | 320.3422 | 320.7930 | 321.2439 | 321.6950 | 322.1463 | 322.5978 | 323.0495 | 323.5013 |
| 323.9533 | 324.4055 | 324.8578 | 325.3104 | 325.7632 | 326.2161 | 326.6692 | 327.1225 | 327.5760 | 328.0296 |
| 328.4835 | 328.9375 | 329.3917 | 329.8461 | 330.3008 | 330.7555 | 331.2104 | 331.6657 | 332.1210 | 332.5765 |
| 333.0323 | 333.4882 | 333.9443 | 334.4007 | 334.8572 | 335.3138 | 335.7708 | 336.2279 | 336.6852 | 337.1426 |
| 337.6003 | 338.0582 | 338.5163 | 338.9746 | 339.4331 | 339.8917 | 340.3506 | 340.8097 | 341.2690 | 341.7285 |
| 342.1882 | 342.6481 | 343.1082 | 343.5685 | 344.0291 | 344.4898 | 344.9507 | 345.4119 | 345.8732 | 346.3348 |
| 346.7966 | 347.2586 | 347.7208 | 348.1832 | 348.6458 | 349.1087 | 349.5717 | 350.0350 | 350.4985 | 350.9622 |
| 351.4262 | 351.8903 | 352.3547 | 352.8193 | 353.2841 | 353.7492 | 354.2145 | 354.6800 | 355.1457 | 355.6117 |
| 356.0779 | 356.5443 | 357.0109 | 357.4778 | 357.9449 | 358.4122 | 358.8798 | 359.3477 | 359.8157 | 360.2840 |
| 360.7525 | 361.2213 | 361.6903 | 362.1595 | 362.6290 | 363.0988 | 363.5687 | 364.0390 | 364.5094 | 364.9802 |
| 365.4512 | 365.9224 | 366.3939 | 366.8656 | 367.3376 | 367.8098 | 368.2824 | 368.7551 | 369.2281 | 369.7014 |
| 370.1750 | 370.6488 | 371.1229 | 371.5973 | 372.0719 | 372.5468 | 373.0220 | 373.4974 | 373.9731 | 374.4491 |
| 374.9254 | 375.4019 | 375.8788 | 376.3559 | 376.8333 | 377.3110 | 377.7890 | 378.2673 | 378.7458 | 379.2248 |
| 379.7039 | 380.1834 | 380.6631 | 381.1432 | 381.6236 | 382.1043 | 382.5853 | 383.0666 | 383.5482 | 384.0302 |
| 384.5124 | 384.9950 | 385.4779 | 385.9612 | 386.4447 | 386.9287 | 387.4129 | 387.8975 | 388.3825 | 388.8677 |
| 389.3533 | 389.8393 | 390.3257 | 390.8124 | 391.2995 | 391.7869 | 392.2747 | 392.7630 | 393.2516 | 393.7405 |
| 394.2299 | 394.7197 | 395.2099 | 395.7005 | 396.1915 | 396.6830 | 397.1749 | 397.6673 | 398.1601 | 398.6534 |
| 399.1471 | 399.6414 | 400.1361 | 400.6313 | 401.1270 | 401.6234 | 402.1202 | 402.6176 | 403.1155 | 403.6141 |
| 404.1133 | | | | | | | | | |

FIG. 4h

METHOD AND DEVICE OF BRAIN'S CARTOGRAPHY IMPLEMENTED BY INTERPOLATION

BACKGROUND OF THE INVENTION

This invention is concerned with a method of interpolation of any quantity in any point of a sphere as well as with a device to determine an said electrical value and a device to display the topography of a potential field.

It is concerned more particularly with tests of functional exploration in neurology consisting in reading out from the electroencephalogram the brain's electric response as caused by applying a physiological stimulation (acoustical, visual, somesthesical stimulation)to the subject. The response is collected by means of several electrodes distributed over the scalp.

In the existing art, a great number of electrodes are used, that are evenly distributed on the whole spherical surface. The evaluation of the measures between two acquisition points is made by methods of interpolation which do not ensure an adequate accuracy.

SUMMARY OF THE INVENTION

This invention is concerned with a method of interpolation that, with only a limited number of electrodes distributed over any points of acquisition, permits one to obtain the value of the field of an electromagnetic quantity, more particularly of a potential field or an electric current, or of a magnetic quantity, for instance, the radial component of the magnetic field.

This invention is concerned more particularly with a method of interpolation of an electric quantity U in any point P of a sphere taken as a model of an upper portion of the head, from a finished number n of measures $z_i = U(P_i)$ carried out in the n determined and known sites $P_i$ consisting in:

storing in a computer memory the polar coordinates $(\theta_i, \phi_i)$ of sites $P_i$, as well as the associated values $z_i$ of the electric signal in a given time t, calculating for the n measure sites $P_i$ the values:

$x_1 = \cos \phi_1$ $y_i = \sin \phi_1$ and $$z_i = \sqrt{1 - x_i^2 - y_i^2} \text{ if } \theta_i \leq \frac{\pi}{2}$$

$$- \sqrt{1 - x_i^2 - y_i^2} \text{ if } \theta_i > \frac{\pi}{2}$$

Calculating for all pairs of measures $(P_1, P_j)$, the distance:

$$d_{ij} = \sqrt{(x_i - x_j)^2 + (y_i - y_j)^2 + (z_i - z_j)^2}$$

and the value:

$$\cos \gamma\, ij = 1 - \frac{d^2\, ij}{2}$$

Calculating the value of the function $k_m (P_i, P_j)$ by reading out the value of the function $k_m$ from a pre-computed table.

Constructing the matrix:

$$\begin{bmatrix} K & E \\ E^t & O \end{bmatrix}$$

where E is vector $(1,1,. \ldots . 1)^t$ and K the matrix of values km $(P_i, P_j)$, Determining the value of coefficients: $P = (p_1, \ldots p_n)$ t and coefficient q by resolution of the equation:

$$\begin{bmatrix} K & E \\ E^t & O \end{bmatrix} \times \begin{bmatrix} P \\ q \end{bmatrix} = \begin{bmatrix} Z \\ O \end{bmatrix}$$

Z being the table $(z_1, \ldots z_n)^t$

Calculating for all points P' of coordinates (X,Y) of the projection plane of the sphere the values:

$$\theta = \sqrt{X^2 + Y^2}$$

$$x = X \frac{\sin \theta}{\theta}$$

$$y = Y \frac{\sin \theta}{\theta}$$

$$Z = \sqrt{1 - x^2 - y^2} \text{ if } \theta \leq \frac{\pi}{2}$$

$$- \sqrt{1 - x^2 - y^2} \text{ if } \theta > \frac{\pi}{2}$$

if the method of radial Projection is adopted,

Determining the coefficient:

$$\cos \gamma(P, P_i) = 1 - \frac{d^2}{2}$$

where $$d = \sqrt{(x - x_i)^2 + (y - y_i)^2 + (z - z_i)^2}$$

Determining km $(\cos \gamma(P,P_i))$ by reading out the value of the function km from a pre-computed table, Calculating the electric value U :

$$U = \sum_{i=1}^{n} P_i \cdot k_m (P, P_i) + q$$

where:

$$k_m(P, P_i) = \frac{1}{4\pi} \sum_{\nu=1}^{\infty} \frac{2\nu + 1}{\nu^m(\nu + 1)^m} [P_\nu \cos\gamma(P, P_i)]$$

and $P_\nu = [^{th}$ Legendre polynomial expansion.

According to a preferred embodiment, there are stored in a computer memory 2001 values of function $k_m$ for $\cos \gamma$ varying from $-1$ to $+1$ and a value $k_m(\cos \gamma)$ is determined by reading out the stored value at the address integer portion of $(1000 \cos \gamma + 1001)$ According to a preferred alternative embodiment, the resolution of the matrix equation:

$$\begin{bmatrix} K & E \\ E^t & O \end{bmatrix} \times \begin{bmatrix} P \\ q \end{bmatrix} = \begin{bmatrix} Z \\ O \end{bmatrix}$$

is obtained by using a symmetrical matrix factorization subroutine with pins on diagonal.

This invention is concerned more particularly with a method of displaying the topography of a potential or magnetical field consisting in:

picking up the signal in a finished number of sites, in interpolating the values of the signal between said sites according to the above-described method, generating for each display pixel a signal representing the corresponding interpolated signal.

The method of the invention permits a prompt processing and representation of the evolution with time of signals picked up on a sphere and interpolated between acquisition sites.

More particularly it permits the display of the evolution with time of the potential field representing the electric response of the brain, as caused by a physiological stimulation.

This invention can be more particularly applied to reconstructing the topography of the potential field alluded to, consisting in:

Placing a finished number of electrodes on the patient's scalp,

Interpolating the potential value for all other points of the topography,

Displaying the value of said potentials on a screen according to a plane projection of scalp.

According to an alternative embodiment, this invention permits the reconstruction of the topography of the radial component of the current density vector in the vicinity of the scalp surface, from the values $z_i$ of electric potentials measured on a finished number of electrodes.

The method consists in:

Storing in a computer memory the polar coordinates $(\theta_i, \phi_i)$ of sites $P_i$, as well as the associated values $z_i$ of the electric signal in a given time t, Calculating for the n measure sites $P_i$ the values;

$x_i = \cos \phi_i$ $y_i = \sin \phi_i$ and $$z_i = \sqrt{1 - x_i^2 - y_i^2} \quad \text{if } \theta_i \leq \frac{\pi}{2}$$
$$- \sqrt{1 - x_i^2 - y_i^2} \quad \text{if } \theta_i > \frac{\pi}{2}$$

Calculating for all pairs of measures $(P_i, P_j)$ the distance:

$$d_{ij} = \sqrt{(x_i - x_j)^2 + (y_i - y_j)^2 + (z_i - z_j)^2}$$

and the value:

$$\cos \gamma_{ij} = 1 - \frac{d^2\, ij}{2}$$

Calculating the value of the function $k_m (P_i, P_j)$ by reading out function $k_m$ from a pre-computed table, Constructing the matrix:

$$\begin{bmatrix} K & E \\ E^t & O \end{bmatrix}$$

where E is vector $(1,1,1, \ldots 1)^t$ and K is the matrix of values $k_m (P_i, P_j)$, Determining the value of coefficients:

$P=(p_1, \ldots p_n)^t$ and coefficient q by resolution of the equation:

$$\begin{bmatrix} K & E \\ E^t & O \end{bmatrix} \times \begin{bmatrix} P \\ q \end{bmatrix} = \begin{bmatrix} Z \\ O \end{bmatrix}$$

Z being the table $(Z_1, \ldots Z_n)t$,

Calculating for all points P' with coordinates (X,Y) of the sphare projection plane the values:

$$\theta = \sqrt{X^2 + Y^2}$$
$$x = X \frac{\sin \theta}{\theta}$$
$$Y = Y \frac{\sin \theta}{\theta}$$
$$Z = \sqrt{1 - x^2 - y^2} \text{ if } \theta \leq \frac{\pi}{2} -$$
$$\sqrt{1 - x^2 - y^2} \text{ if } \theta > \frac{\pi}{2}$$

Calculating the value of the radial component of the vector:

$$J_m(p) = - \sum_{i=1}^{n} p_i h_m (P, P_i)$$

with, in this case:

$$h_m(P, P_i) = \frac{1}{4\pi} \sum_{\nu=1}^{\infty} \frac{2\nu + 1}{\nu^{m-1}(\nu + 1)^{m-1}} P_\nu [\cos\gamma (P, P_i)]$$

$h_m$ being read out from a pre-computed table

This invention also relates to a device for determining the value of an electric signal in any site of a sphere, comprising processing circuits for the electric signal picked up in a finished number of acquisition sites, a computer provided with memory means controlled by a program that utilizes the above-described method, as well as display means for the value of the electric signal relevant to the site under consideration.

The device of the invention is more particularly destined to displaying a potential field that is representative of an electroencephalographic parameter comprising processing circuits for the signal picked up by a finished number of electrodes, a computer controlled by a program for computing the interpolation values according to the process of the invention, memory and display means.

BRIEF DESCRIPTION OF THE DRAWINGS

Other advantages and modes of embodiment will appear from the following description, with reference to drawings where.

DETAILED DESCRIPTION OF THE INVENTION

Figure 1:
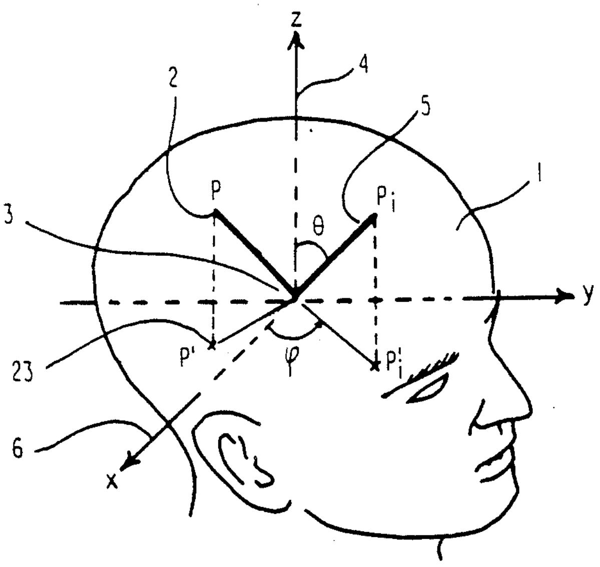
FIG. 1 is a perspective view of a scalp and a measure site $P_i$ and of a point P where an estimation of the value of the measure is desired.
Figure 5:
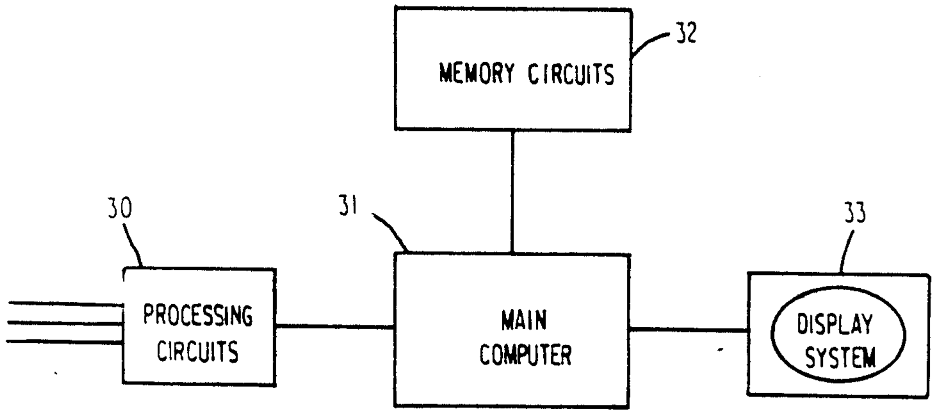
FIG. 5 is the principle diagram of a device for the implementation of the invention.

A certain number of values $z_i$ measured on sites $P_i$ distributed on a patient's scalp assimilated to a sphere, as shown in FIG. 1, are available.

Readings are picked up by electrodes the number of which ranges from 16 to 32 for instance, and that are distributed over points $P_i$ of scalp 1.

The problem to be solved is to make an evaluation of the value U of the electric signal at any point P, 2,of scalp 1 as a function of the values $U(P_i)$ read and eventually to project the data onto a plane in order to display the topographic distribution of the values calculated.

Points $P_i$ of scalp 1 are identified by their polar coordinates $(\theta,\phi)$, $\theta$ representing the angle formed by the vector joining the centre of sphere 3 with point $P_i$ with an axis called OZ, 4 and $\phi$ representing the angle formed by the projection of vector OP, 5, in the XOY plane perpendicular with OZ, with an axis designed as OX, 6. OZ, 4, can be oriented in any direction. In FIG. 1, the direction is a vertical one and the axis passes through the top of the head.

The process of the invention consists in an interpolation based on the measure positions $P_i$ $(\theta_i, \phi_i)$ and the associated values $z_i$, to evaluate the value U associated with any point P on the sphere surface.

The projection plane XOY is divided into a matrix of elementary squares intended to represent a pixel on a computer screen. The center of each elementary square will represent a point P' of the (XOY) plane.

Figure 2:
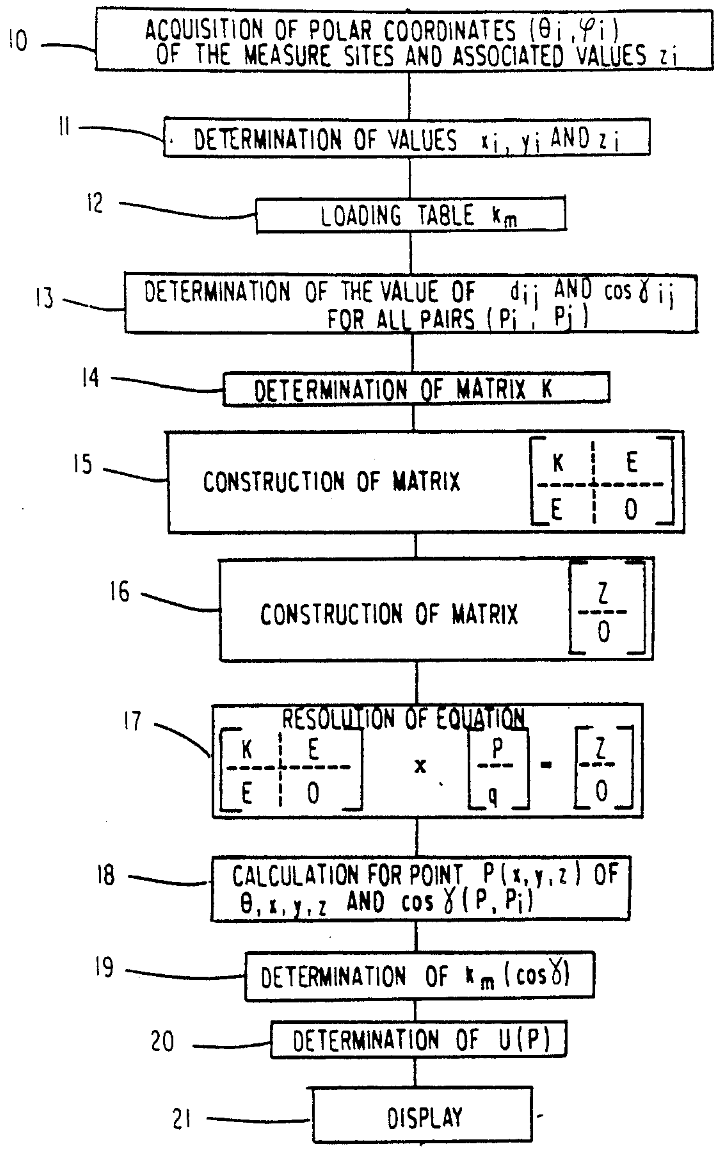
FIG. 2 is the organigram of the implementation program of the process, FIGS. 3a—3h collectively show the pre-computed table of values $k_m$, FIGS. 4a—4h collectively show a the pre-computed table of values $h_m$.

The process consists first in the acquisition of the coordinates of all measure points as well as the associated measure values $Z_i$. This operation corresponds to stage 10 of the algorithm shown in FIG. 2.

Stage 11 consists in determining the values $x_i$, $y_i$, and $z_i$ of measure sites where:

$x_i = \cos\phi_i$ $y_i = \sin\phi_i$ and $$z_i = \sqrt{1 - x_i^2 - y_i^2} \text{ if } \theta \leq \frac{\pi}{2}$$
$$-\sqrt{1 - x_i^2 - y_i^2} \text{ if } \theta > \frac{\pi}{2}$$

Stage 12 consists in loading the km value table in the computer memory. This can be made at any time of the algorithm.

$$km(P, P_i) = \frac{1}{4\pi} \sum_{\nu=1}^{\infty} \frac{2\nu + 1}{\nu^m (\nu + 1)^m} \times P_\nu [\cos\gamma(P, P_i)]$$

where P is the $\nu$th Legendre polynomial expansion and $(P, P_i)$ is the angle formed by vectors OP and $OP_i$.

In order to reduce the volume of calculations and therefore accelerate the procedure of image synthesis, it is advantageous to pre-calculate the $k_m$ values in function of cos $\gamma$ and to store them in a memory:

By way of example, FIGS. 3a–3h collectively show shows a table comprising 2001 values of $k_m$ for cos $\gamma$ varying from −1 to +1.

Stage 13 consists in determining the value $d_{ij}$ for each of the measure sites $(P_i, P_j)$:

$$d_{ij} = \sqrt{(x_i - x_j)^2 + (y_i - y_j)^2 + (z_i - z_j)^2}$$

as well as the value $$\cos\gamma_{ij} = 1 - \frac{d_{ij}^2}{2}$$

Stage 14 consists in determining the matrix K of values $k_{ij}$.

The value $k_{ij}$ is determined by reading out the value $k_m$, the address of which corresponds to the integer portion of $(1000 \cos\gamma_{ij} + 1001)$.

Eventually, the $k_{ij}$ value can be affined by a linear extrapolation between two values of the table when $1000 \cos\gamma_{ij}$ is not integer.

Stage 15 consists in constructing a matrix:

$$\left[\begin{array}{c|c} K & E \\ \hline E^t & 0 \end{array}\right]$$

where K is the matrix of values $k_{ij}$, E is the table $(1,1, \ldots 1)^t$

Stage 16 consists in constructing a matrix:

$$\left[\begin{array}{c} Z \\ \hline 0 \end{array}\right]$$

where Z is the vector of measure values $z_i$.

Stage 17 consists in resolving the matrix equation:

$$\left[\begin{array}{c|c} K & E \\ \hline E^t & O \end{array}\right] \times \left[\begin{array}{c} P \\ \hline q \end{array}\right] = \left[\begin{array}{c} Z \\ \hline O \end{array}\right]$$

The resolution of the matrix equation can be obtained by means of a symmetrical matrix factorization routines with pins on diagonal. In particular the SSFPA and SSPSL routines of LINPACK software can be used.

Stage 18 consists in calculating for a point P, 2, with cartesian coordinates (x, y, z), the values $\theta$, x, y, z and cos $\gamma(P, P_i)$ where (X,Y) are the coordinates of the projection P', 23, of point P, 2 on the projection plane XOY and relevant to the centre of a display pixel on a screen. If, for instance, P' is obtained via a radial projection:

$$\theta = \sqrt{X^2 + Y^2}$$
$$x = X\frac{\sin\theta}{\theta}$$
$$y = Y\frac{\sin\theta}{\theta}$$
$$z = \sqrt{1 - x^2 - y^2} \text{ if } \theta \leq \frac{\pi}{2}$$
$$-\sqrt{1 - x^2 - y^2} \text{ if } \theta > \frac{\pi}{2}$$

-continued $$\cos\gamma(P, P_i) = 1 - \frac{d^2}{2}$$

where $$d^2 = \sqrt{(x - x_i)^2 + (y - y_i)^2 + (z - z_i)^2}$$

Throughout the description, it is considered that coordinates are determined within a normed system, the distance between any point of scalp 1 and the centre 0, 3, being normed to 1.

Stage 18 consists in determining the value of $k_m$ (P, $P_i$) by reading out the value $k_m$ (cos $\gamma$(P,$P_i$) according to the above-described method of by calculation.

Stage 19 consists in determining the interpolation function $U_m$(P), where:

$$U_m(p) = \sum_{i=1}^{n} p_i \times k_m(P, P_i) + q$$

$P_i$ and q being the solutions of the matrix equation solved at stage 17.

This method of interpolation of an electric signal will be used to represent the topographic distribution of a quantity read on sites distributed over the patient's scalp.

This invention also relates to a device for the implementation of the above-described method.

The device more particularly comprises processing circuits 30 for the electric signals acquired on the measure sites. These circuits may more particularly comprise amplifiers, digitizers and suppressor systems for background noise and other interferences.

The processed signals are transmitted to a main computer 31 comprising memory circuits 32.

The memory circuits 32 are more particularly destined to store the pre-computed values $k_m$ as well as the coordinates of the measure sites $P_i$.

The computer 31 is driven by a program designed to implement the method of the invention.

A display system 33 — screen on plotting table — permits a representation of the signal topography together with its evolution with time.

This invention is not restricted to the modes of embodiment and examples of application and utilization that are described in the foregoing but on the contrarY it comprises all alternative embodiments.

What is claimed is:

1. A device for the determination of the value of an electrical quantity $U_m$(P) at any particular site P of a sphere, based on measurements $Z_i$ of said electrical quantity made at known sites $P_i$ on said sphere, said device comprising:

measuring means for measuring the values $Z_i$ of said electrical quantity at n said sites $P_i$ having polar coordinates ($\theta_i$, $\phi_{il}$ ) *and cartesian coordinates* ($x_i$, $y_i$, $z_i$) with respect to X, Y and Z axes, respectively, where n is an integer, i is an integer between 1 and n, $\theta_i$ is an angle formed with respect to said Z axis by a vector joining a center of said sphere with a site $P_i$, and $\phi_i$ is an angle formed with respect to said X axis by a projection, into a projection plane containing said X and Y axes, of a vector joining said center of said sphere with said particular site P;

a storage memory for storing coordinates ($\theta_i$, $\phi_i$) and associated measured values $Z_i$ of said electrical quantity;

a computer for (1) calculating for the n sites $P_i$ the values:

$x_i$=cos $\phi_i$ $y_i$=sin $\theta_i$ $$z_i = \sqrt{1 - x_i^2 - y_i^2} \quad \text{if } \theta_i \leq \frac{\pi}{2}$$
$$- \sqrt{1 - x_i^2 - y_i^2} \quad \text{if } \theta_i > \frac{\pi}{2}$$

(2) calculating for all pairs of said n sites ($P_i$, $P_j$), where i and j are integers between 1 and n:

$$d_{ij} = \sqrt{(x - x_i)^2 + (y - y_i)^2 + (z - z_i)^2}$$

$$\text{and } \cos\phi_{ij} = 1 - \frac{d_{ij}^2}{2}$$

(3) generating a vector K of values $k_{ij}$ of a function $k_m$ (cos$\phi_{ij}$) for each of said pairs of sites ($P_i$, $P_j$) by reading out the value of the funtion $k_m$ from a pre-computed table, (4) constructing the matrix:

$$\left[\begin{array}{c|c} K & E \\ \hline E^t & O \end{array}\right]$$

where E is a table (1,1, . . . . 1)$^t$, (5) determining the value of coefficients P=($p_i$, . . . $p_n$)$^t$ and the value of a variable q by resolution of the matrix:

$$\left[\begin{array}{c|c} K & E \\ \hline E^t & O \end{array}\right] \times \left[\begin{array}{c} P \\ \hline q \end{array}\right] = \left[\begin{array}{c} Z \\ \hline O \end{array}\right]$$

where Z is a table ($Z_1$, . . . $Z_n$)$^t$ of measured values $Z_i$, (6) computing, for all points P' of coordinate (X,Y) of said projection plane, the values, in the case of a radial type projection mode:

$$\theta = \sqrt{X^2 + Y^2}$$

$$x = X\frac{\sin\theta}{\theta}$$

$$y = Y\frac{\sin\theta}{\theta}$$

$$z = \sqrt{1 - x^2 - y^2} \quad \text{if } \theta \leq \frac{\pi}{2} -$$
$$\sqrt{1 - x^2 - y^2} \quad \text{if } \theta > \frac{\pi}{2}$$

(7) determining the coefficient:

cos $\phi$ (P,$P_i$) =1−$d^2$/2

$$\cos\phi(P, P_i) = \frac{1 - d^2}{2}$$

(8) determining the variable $k_m$ (cos $\phi$) by reading out the value of the function $k_m$ from a pre-computed table, and (9) calculating the value:

$$U_m(P) = \sum_{i=1}^{n} p_i \cdot k_m + q$$

corresponding to the value of the electric signal at said particular point P; and display means for displaying said calculated value of $U_m(P)$.

2. A device according to claim 1, further comprising a second storage memory for storing the values of the function $k_m(\cos\phi)$ as pre-computed for $\cos\phi$ ranging from $-1$ to $+1$.

3. A device according to claim 2, characterized in that the computer further determines a value $h_m(P, P_i)$ by reading out values of the function $h_m$ from a pre-computed table and computes the radial component of the current density vector:

$$J_m(P) = -\sum_{i=1}^{n} P_i \cdot h_m(P, P_i).$$

4. A device according to claim 1, characterized in that the computer further determines a value $h_m(P, P_i)$ by reading out the values of the function $h_m$ from a pre-computed table and computes the radial component of the current density vector:

$$J_m(P) = -\sum_{i=1}^{n} P_i \cdot h_m(P, P_i).$$

5. A device for the display of the topography of the potential field representing an electroencephalographic parameter in accordance with measurements of electrical signals at various locations over a scalp, said device comprising:

processing circuits for processing signals $Z_i$ picked up by a plurality of electrodes placed over the scalp at n sites $P_i$ having polar coordinates $(\theta_i, \phi_i)$ and cartesian coordinates $(x_i, y_i, z_i)$ with respect to X, Y and Z axes, respectively, where n is an integer, i is an integer between 1 and n, $\theta_i$ is an angle formed with respect to said Z axis by a vector joining a center of said sphere with a site $P_i$, and $\phi_i$ is an angle formed with respect to said X axis by a projection, into a projection plane containing said X and Y axes, of a vector joining said center of said sphere with said particular site P;

a computer driven by a program for (1) calculating for the n sites $P_i$ the values:

$x_i = \cos\phi_i$ $y_i = \sin\theta_i$ $$z_i = \sqrt{1 - x_i^2 - y_i^2} \quad \text{if } \theta_i \leq \frac{\pi}{2}$$
$$- \sqrt{1 - x_i^2 - y_i^2} \quad \text{if } \theta_i > \frac{\pi}{2}$$

(2) calculating for all pairs of said n site $(P_i, P_j)$, where i and j are integers between 1 and n:

$$d_{ij} = \sqrt{(x - x_i)^2 + (y - y_i)^2 + (z - z_i)^2}$$

$$\text{and } \cos\phi_{ij} = 1 - \frac{d_{ij}^2}{2}$$

(3) generating a vector K of values $k_{ij}$ of a function $k_m(\cos\phi_{ij})$ for each of said pairs of sites $(P_i, P_j)$ by reading out the value of the function $k_m$ from a pre-computed table, (4) constructing the matrix:

$$\begin{bmatrix} K & E \\ E^t & O \end{bmatrix}$$

where E is a table $(1, 1, \ldots, 1)^t$, (5) determining the value of coefficients $P = (p_i, \ldots p_n)^t$ and the value of a variable q by resolution of the matrix:

$$\begin{bmatrix} K & E \\ E^t & O \end{bmatrix} \times \begin{bmatrix} P \\ q \end{bmatrix} = \begin{bmatrix} Z \\ O \end{bmatrix}$$

where Z is a table $(Z_1, \ldots Z_n)^t$ of measured values $Z_i$, (6) computing for all points P' of coordinate (X,Y) of said projection plane of the values, in the case of a radial type projection mode:

$$\theta = \sqrt{X^2 + Y^2}$$

$$x = X\frac{\sin\theta}{\theta}$$

$$y = Y\frac{\sin\theta}{\theta}$$

$$z = \sqrt{1 - x^2 - y^2} \quad \text{if } \theta \leq \frac{\pi}{2} -$$
$$\sqrt{1 - x^2 - y^2} \quad \text{if } \theta > \frac{\pi}{2}$$

(7) determining the coefficient:

$$\cos\phi(P, P_i) = \frac{1 - d^2}{2}$$

(8) determining the variable $k_m(\cos\phi)$ by reading out the value of the function $k_m$ from a pre-computed table, and (9) calculating the value:

$$U_m(P) = \sum_{i=1}^{n} p_i \cdot k_m + q$$

corresponding to the value of the electric signal at said particular point P; and display means for displaying the topography of values $U_m(P)$ determined by said computer on a plane projection of said scalp.

6. A device according to claim 5, characterized in that said computer further comprises a storage memory of the values of the function $k_m(\cos\phi)$ as pre-computed for $\cos\phi$ ranging from $-1$ to $+1$.

7. A device according to claim 5, characterized in that the computer further determines a value $h_m(P, P_i)$ by reading out values of the function $h_m$ from a pre-computed table and computes the radial component of the current density vector:

$$J_m(P) = -\sum_{i=1}^{n} P_i \cdot h_m(P, P_i).$$

* * * * *